United States Patent [19]
Mimoun

[11] Patent Number: 6,046,127
[45] Date of Patent: *Apr. 4, 2000

[54] PROCESS FOR THE PREPARATION OF ALCOHOLS

[75] Inventor: Hubert Mimoun, Challex, France

[73] Assignee: Firmenich SA, Geneva, Switzerland

[*] Notice: This patent is subject to a terminal disclaimer.

[21] Appl. No.: 09/115,738

[22] Filed: Jul. 15, 1998

Related U.S. Application Data

[62] Division of application No. 08/646,306, May 15, 1996, Pat. No. 5,831,133.

[30] Foreign Application Priority Data

Oct. 19, 1994 [CH] Switzerland ............................. 3138/94
Feb. 16, 1995 [CH] Switzerland ............................. 445/95

[51] Int. Cl.$^7$ ............................. B01J 31/00; C07C 29/14
[52] U.S. Cl. ........................... 502/170; 568/814; 568/880; 568/881
[58] Field of Search ..................................... 568/814, 880, 568/881; 502/170

[56] References Cited

U.S. PATENT DOCUMENTS

| | | | |
|---|---|---|---|
| 3,061,424 | 10/1962 | Nitzsche et al. | 75/108 |
| 4,868,345 | 9/1989 | Drent | 568/885 |
| 5,196,601 | 3/1993 | Kitsuki et al. | 568/817 |
| 5,220,020 | 6/1993 | Buchwald et al. | 544/106 |
| 5,227,538 | 7/1993 | Buchwald et al. | 568/814 |
| 5,831,133 | 11/1998 | Mimoun | 568/814 |

OTHER PUBLICATIONS

Barr et al., "Titanocene–Catalyzed Reduction of Esters Using Polymethylhydrosiloxane as the Stoichiometric Reductant", *J. Org. Chem.*, vol. 59, No. 15 (1994), pp. 4323–4326.

Boyer et al., "Reduction Selective de Composes Carbonyles par Catalyse Heterogene a la Surface des Sels", *Tetrahedron*, vol. 37 (1981), pp. 2165–2171.

Grady et al., "A Simple Technique for Performing Reactions with Organotin Hydrides", *J. Org. Chem.*, vol. 6, No. 6 (1969), pp. 2014–2016.

Lipowitz et al., "Use of Polymethylhydrosiloxane as a Selective, Neutral Reducing Agent for Aldehydes, Ketones, Olefins, and Aromatic Nitro Compounds", *J. Org. Chem.*, vol. 38, No. 1 (1973), pp. 162–165.

Lipowitz et al., "The Use of Polymethylhydrosiloxane (PMHS) as a Reducing Agent for Organic Compounds", *Aldrichim. Acta*, 6, 1 (1973), pp. 1–6.

Nitzsche et al., "Reduktionen mit Methyl–wasserstoff–polysiloxanen", *Angewandte Chemie*, vol. 69 (1957), p. 69.

Matlin et al., "An Immobilized Organotin Catalyst for Reduction of Ketones and Aldehydes", *J. Chem. Soc., Chem. Commun.*, No. 12 (1984), pp. 798–799.

*Primary Examiner*—Jose' G. Dees
*Assistant Examiner*—Barbara Badio
*Attorney, Agent, or Firm*—Pennie & Edmonds LLP

[57] ABSTRACT

Aldehydes, ketones, esters and lactones may be reduced using a reductant system consisting of a silane derivative and a metal hydride to give good yields of the corresponding alcohols. The reductant system used in the method enables preferential reduction of the carbonyl function. In one embodiment, the reductant system consists of polymethylhydroxysilane and a metal hydride, the hydride being prepared in situ or ex situ from a metal salt or complex by means of a reaction with a reducing agent.

40 Claims, No Drawings

PROCESS FOR THE PREPARATION OF ALCOHOLS

This appliction is a divisional of U.S. application Ser. No. 08/646,306 filed May 15, 1996, now U.S. Pat. No. 5,831,133.

TECHNICAL FIELD AND PRIOR ART

The reduction of carbonyl compounds such as aldehydes, ketones, esters or lactones is a choice reaction for the general preparation of alcohols. In this context, the reduction of the carbonyl function in the compounds having other unsaturated groups in the molecule, such as ethylenic or acetylenic carbon-carbon functions, presents some difficulties due to the generally poor selectivity of catalytic hydrogenation methods via hydrogen. The same applies to the reduction of carbonyl compounds having a defined spatial configuration. In fact, the use of ordinary catalysts such as copperchromites, which only operate at elevated temperatures and pressures, leads to the reduction of the other functionalities present and in many cases, to a modification of the stereochemistry.

In the case of the reduction of unsaturated carbonyl compounds, only lithium aluminium hydride has the property of reducing at once aldehydes, ketones and esters in smooth reaction conditions, while being inert towards unsaturated carbon-carbon bonds eventually present in the molecule. Sodium borohydride or $NaAlH_2(OCH_2CH_2OCH_3)_2$, [Vitride®], also used to promote the carbonyl function reduction, are weakly reactive towards esters. All these reagents, the use of which requires stoechiometric amounts, show the major drawback of being sensitive to moisture and air; furthermore, these reagents are very costly and pollutant, leading to the necessity of developping more economical and easier to handle systems.

It is noteworthy that the polymethyl-hydroxysilane (PMHS), which is defined by the following general formula:

$$(CH_3)_3-SiO(CH_3HSiO)_nSi(CH_3)_3$$

n being an integer indicating the number of repeated units, can promote the reduction of aldehydes to alcohols when in the presence of tin based catalysts [see Nizsche and Wick, Angew. Chem. 1957, 69, 996 and U.S. Pat. No. 3,061,424].

Grady and Kuivila (J. Org. Chem. 1969, 34, 2014) and Lipowitz and Bowman (Aldrichim. Acta 1973, 6, 1 and J. Org. Chem. 1975, 33, 162) have shown that, for the reducing system PMHS, the tin catalysis could be applied to the reduction of aldehydes and ketones, but not to that of esters into alcohols.

U.S. Pat. No. 5,220,020 describes a method for the preparation of alcohols by reduction of carbonyl compounds by means of a system constituted by a silanic reducing agent and a metal catalyst of formula $$M(L)(L')(L'') \text{ to } M(L)(L')(L'')(L''')(L^{IV})(L^V)$$

wherein M is a metal belonging to group 3, 4, 5 or 6, a lanthanide or an actinide, whereas (L') to ($L^V$) represent hydrogen, an alkyl, an aryl, a silyl, a halogen, or a radical —OR, —SR or —N R(R'), wherein R and R' are hydrogen, an alkyl or an aryl. Such a system could be applied to the reduction of esters, lactones, amides and imides.

Among the preferred catalysts, the patent above-cited mentions titane (IV) isopropylate and ethylate, as well as trichlorotitane (IV) isopropylate.

More recently Barr, Berk and Buchwald (J. Org. Chem. 1994, 59, 4323) have shown that the complex $Cp_2TiCl_2$ reduced by butyllithium or ethylmagnesium bromide could catalyse the reduction of esters to the corresponding alcohols with good yields, but this technique requires expensive catalytic reagents, which are difficult to use on a large scale in the context of an industrial preparation.

DESCRIPTION OF THE INVENTION

We have now discovered that it was possible to prepare alcohols in good yields and in an economical way, by reduction of carbonyl derivatives such as aldehydes, ketones, esters and lactones, by means of polymethyl-hydroxysiloxane hydride, in the presence of a catalyst which can be prepared in situ or separately, from a metallic salt or complex and a reducing agent.

The process of the invention presents the advantage of employing inexpensive reagents, the use of which requires no particular precautions regarding protection against moisture or air. We have also ascertained that the reducing system of the invention does not lead to agglomeration or caking of the reaction medium, as opposed to what we were able to observe with the prior art systems.

The object of the present invention is therefore a process for the preparation of alcohols by reduction of the carbonyl function in substrates belonging to the class of aldehydes, ketones, esters or lactones, which may or may not contain unsaturated functions other than the carbonyl group, which is characterized in that:

a. the carbonylated substrate is reacted with stoechiometric amounts of a silanic agent in the presence of a catalyst prepared from a metallic salt or complex and a reducing agent, b. the obtained siloxane is hydrolysed by means of a basic agent, and c. the desired alcohol thus formed is separated and purified.

The reaction which characterizes the process of the invention is illustrated by the following schemes:

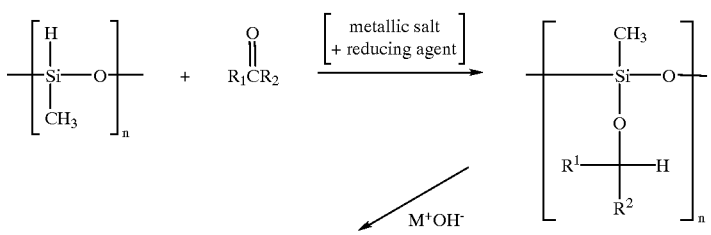

-continued

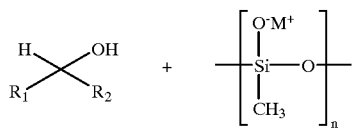

for aldehydes and ketones, and

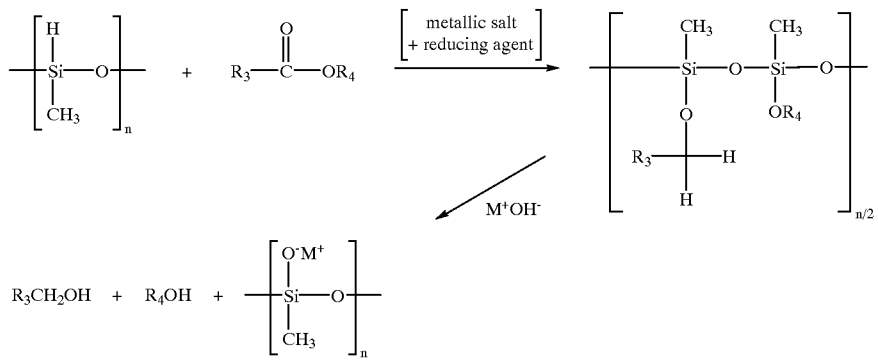

$R_3CH_2OH + R_4OH +$ [structure]

for esters and lactones.

PREFERRED EMBODIMENT OF THE INVENTION

Trialkylsilanes, dialkylsilanes, trialkoxysilanes or polymethyl-hydroxysilane (PMHS) can be used as the silanic agent.

Thus, dimethylsilane, diethylsilane, trimethoxysilane, triethoxy-silane or PMHS will be preferably used. The latter silanic derivative is preferably used owing to its efficiency and availability.

The catalyst according to the invention can be obtained in situ, in the reaction medium or be prepared separately from a metallic salt or complex of general formula $MX_n$, wherein M represents a transition metal selected amongst zinc, cadmium, manganese, cobalt, iron, copper, nickel, ruthenium and palladium, X an anion such as a halide, a carboxylate or any anionic ligand, and n a number comprised between 1 and 4. To this end, there can be used a chloride, bromide, iodide, carbonate, isocyanate, cyanide, sulfate, phosphate, acetate, propionate, 2-ethylhexanoate, stearate or naphthenate of one of the above-mentioned metals, which will be reacted with a reducing agent such as a hydride, in order to generate the active catalyst according to the process of the invention.

For this purpose, an alkaline hydride such as lithium, sodium or potassium hydride, or an alkaline earth hydride such as magnesium or calcium hydride will be used. A boron hydride such as $BH_3$, a metallic borohydride $M+BH_4$ ($M^+$= Li, Na, K) or $M(BH_4)_2$ (M=Mg, Zn, Ca), an alkylborane $R_nBH_{(4-n)}M$ (R=alkyl, n=1 to 3, M=alkaline metal), an alkoxyborane $(RO)_nBH_{(4-n)}M$ (R=alkyl, n=1 to 3, M=alkaline metal), an aluminium hydride $AlH_3$, $AlH_nR_{3-n}$ (R=alkyl), $MAlH_4$ (M=Li, Na, K), $MAlH_n(OR)_{4-n}$ (M=Li, Na, K), an organic magnesium compound of formula RMgX (R=alkyl, X=Cl, Br, I), an organic lithium compound RLi (R=alkyl, for example $C_1$ to $C_4$ or aryl), can also be used.

We observed that it could be advantageous, especially when the catalyst is prepared ex situ, to add to the catalytic system consisting of metallic salt and reducing agent a ligand able to complex the formed metallic hydride and, therefore, to better solubilize said hydride in the organic phase. As the ligand, an alcohol ether such as methoxyethanol, or an alcohol amine such as dimethylaminomethanol, diethanolamine or triethanolamine, can be used.

According to a particular embodiment of the invention, a stable and homogeneous catalytic solution can for instance be formed by reacting, in an inert organic solvent, for example toluene, tetrahydrofuran or isopropyl ether, one equivalent of zinc 2-ethylhexanoate with two equivalents of Vitride® and one equivalent of dimethylaminoethanol. The reaction is characterized by hydrogen release. Once this release is finished, a homogeneous concentrated solution is obtained, which can be stocked for use in the process of the invention.

The concentration of the [metallic salt+reducing agent] system, expressed in molar % of metal relative to the substrate, is generally comprised between 0.1 and 10%, preferably between 1 and 5%.

On the other hand, the molar ratio of the reducing agent relative to the metal is generally comprised between about 1 and 2.

When the catalytic system is prepared in situ, the chosen metallic derivative will be reacted with the reducing agent, in an appropriate solvent. After complete release of the formed hydrogen, the carbonylated substrate to be reduced will be introduced and the silanic agent added into the solution.

The typical consumption for example of PMHS will be of 2 equivalents for the reduction of esters or lactones and of 1 equivalent for reduction of aldehydes or ketones. The alcohol obtained as the product of the reduction can be separated by hydrolysis of the obtained siloxane, which hydrolysis can be accomplished by reacting the reaction medium with an aqueous or alcoholic solution of a basic agent, such as for example caustic soda (sodium hydroxide), potash (potassium hydroxide), lime (calcium oxide) or sodium carbonate. The proportion of base relative to the PMHS is comprised between 1 and 2 molar equivalents. Once the hydrolysis is complete, formation of two phases is generally observed. The desired alcohol being in the organic phase, it can be obtained by simple evaporation of the solvent, with the possibility of submitting the residue obtained to a distillation for subsequent purification.

As indicated above, one of the advantages of the process of the invention is that it does not lead to any caking, and that it is possible to operate without solvent in a very concentrated solution. However, in order to better control the reaction temperature (exothermic), we prefer to operate with a solvent.

As appropriate solvent, an ether such as methyltertbutylether, diisopropylether, dioxane, tetrahydrofuran, ethyleneglycoldimethylether can be used. An aliphatic hydrocarbon such as heptane, petroleum ether, octane, cyclohexane, or aromatic as benzene, toluene, xylene or mesitylene, can also be used.

As indicated above, the process of the invention allows the reduction of various carbonylated compounds, having or not unsaturations other than the carbonyl, for example olefinic, acetylenic functions or nitrile groups, which groups are not, or are little affected by the reduction.

As example of aldehydic substrates, butanal, pentanal, hexanal, heptanal, octanal, decanal, dodecanal, either in linear or branched form, can be cited. Other unsaturated aldehydes susceptible of being reduced into corresponding unsaturated alcohols are acroleine, methacroleine, crotonaldehyde, prenal, citral, retinal, campholenic aldehyde, cinnamic aldehyde, hexylcinnamic aldehyde, formyl pinane and nopal. The aromatic aldehydes such as benzaldehyde, cuminic aldehyde, vanilline, salicylic aldehyde, are also easily reduced into the corresponding alcohols.

As examples of saturated or unsaturated ketones susceptible of being reduced by the silanic reducing agents in the process according to the invention, there can be cited, in a non-limiting manner, hexan-2-one, octan-2-one, nonan-4-one, dodecan-2-one, methyl vinyl ketone, mesityl oxyde, acetophenone, cyclopentanone, cyclohexanone, cyclododecanone, cyclohex-1-en-3-one, isophorone, oxophorone, carvone and camphor.

As non-restrictive examples of esters and lactones susceptible of being reduced by silanic agents according to the process of invention, acetates, propionates, butyrates, isobutyrates, alkyl or aryl benzoates, acrylates, alkyl or aryl crotonates, alkyl cinnamates, methyl cis-3-hexenoate, methyl sorbate, methyl salicylate, methyl 10-undecylenate, methyl oleate, methyl linoleate, methyl linolenate or any mixture of natural fatty acid esters, caprolactone, butyrolactone, dodecalactone, diketene and sclareolide can be cited.

Esters able to be reduced according to the process of the invention also include the triglycerides of fatty acids, such as those which constitute the vegetable or animal oils. When a mixed triglyceride derived from distinct fatty acids is reduced, the corresponding saturated or unsaturated alcohols can thus also be obtained simultaneously, according to the following reaction scheme:

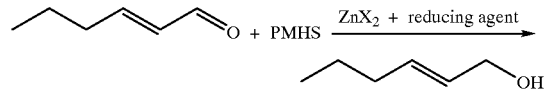

$$R^1\text{---}CH_2OH + R^2\text{---}CH_2OH + R^3\text{---}CH_2OH$$

The substituents $R^1$, $R^2$, and $R^3$ are generally identical or different hydrocarbon rests which can contain 1 to 20 carbon atoms. When these rests present some ethylenic unsaturations of defined configuration, the resulting alcohols will preserve the same stereochemistry. Thus, oils rich in linoleic and linolenic acid, such as linseed oils, will be converted to a mixture enriched in linoleic and linolenic alcohols, whereas the conventional hydrogenolysis of vegetable oils by gaseous hydrogen at high temperature and pressure in the presence of catalysts will be translated into a modification of the double bonds stereochemistry and position in the corresponding alcohols.

Trioleine, peanut oil, sunflower oil, soya oil, olive oil, colza oil, sesame oil, linseed oil, cotton oil, copra oil, grape seeds oil, coconut oil and palm oil, for example, are used as triglycerides which can be reduced by the process of the invention.

The temperature of the reaction is variable and comprised between 0° C. and 150° C., according to the reactivity of the substrate. More generally, we operate between about 50° C. and 110° C.

The invention is illustrated by the following examples, wherein the temperatures are indicated in degrees centigrade, the yields in molar %, and the abbreviations have the usual meaning in the art.

Reduction of aldehydes

EXAMPLE 1

Reduction of trans-hexen-2-al-1

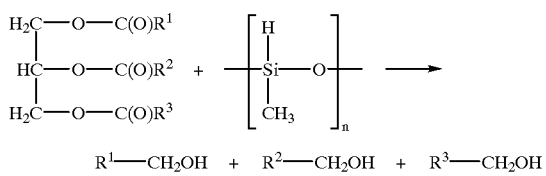

A three-neck flask of 1 l was charged with 50 g of isopropyl ether, 1.5 g of solid sodium borohydride (0.04 mole), then 11.3 g of zinc 2-ethylhexanoate (0.04 mole) and the mixture was stirred for 15 minutes until the hydrogen release stops. Then 196 g (2 mole) of trans hex-2-en-1-al are introduced, and the reaction is taken to reflux. 147 g of PMHS (2.3 mole) are then introduced in 2 h. The reaction is stirred for 2 additional hours until the GC control indicates that all the substrate has disappeared. The mixture is then cooled to 20°, 100 g of water are added, then slowly 460 g of a 30% aqueous sodium hydroxide, without letting the temperature of the reaction mixture increase above 40°.

The mixture is decanted, the aqueous phase containing the sodium silicate is separated, then the organic phase is washed with 100 ml of water saturated with salt, then with 50 g of a 30% aqueous solution of acetic acid. The solvent is evaporated and 211 g of residue are obtained, which residue gives by distillation 188 g of trans hex-2-en-1-ol with a purity above 95%.

EXAMPLE 2 to 13

These are intended to illustrate the influence of the catalytic system and of solvent over the reduction of trans hex-2-en-1-al to trans hex-3-en-1-ol by PMHS. We proceed as described in example 1, but with 10 times lower amounts. The solvent, the zinc salt (2% molar relative to the substrate), the reducing agent (2% molar), then the trans hex-2-en-1-al are charged. Then 1.1 equivalent of PMHS is added to the mixture in 1 h and reflux maintained until total consumption of the substrate. Hydrolysis with 30% sodium hydroxide is then carried out, then the alcohol formed is recovered as in example 1. It has been ascertained that most of the zinc salts used ($ZnCl_2$, $Zn(2\text{-ethyl-hexanoate})_2$, $ZnBr_2$, $ZnEt_2$) in combination with a reducing agent (LiH, NaH, $NaBH_4$, $LiAlH_4$, Vitride®) are active in the reduction of hex-2-en-1-al. In no case did we observe isomerisation of the alcohol formed, nor the

| Examples | Solvent | Zinc salt 2% molar | Reducing agent 2% molar | Reaction time | Yield (%) in hex-3-en-1-ol |
|---|---|---|---|---|---|
| 2 | methyl tert-butyl ether | $ZnCl_2$ | $NaBH_4$ | 5 h | 91% |
| 3 | isopropyl ether | $ZnCl_2$ | $NaBH_4$ | 4 h | 94% |
| 4 | isopropyl ether | Zn(2-ethyl-hexanoate)$_2$ | $NaBH_4$ | 5 h | 90% |
| 5 | isopropyl ether | Zn(2-ethyl-hexanoate)$_2$ | LiH | 6 h | 90% |
| 6 | isopropyl ether | Zn(2-ethyl-hexanoate)$_2$ | NaH | 6 h | 78% |
| 7 | toluene | Zn(2-ethyl-hexanoate)$_2$ | $NaBH_4$ | 4 h | 88% |
| 8 | tetrahydrofuran | Zn(2-ethyl-hexanoate)$_2$ | $NaBH_4$ | 5 h | 87% |
| 9 | isopropyl ether | $ZnBr_2$ | $NaBH_4$ | 6 h | 77% |
| 10 | isopropyl ether | Zn(2-ethyl-hexanoate)$_2$ | $LiAlH_4$ | 4 h | 90% |
| 11 | isopropyl ether | Zn(2-ethyl-hexanoate)$_2$ | $LiAlH_4$ | 4 h | 89% |
| 12 | isopropyl ether | Zn(2-ethyl-hexanoate)$_2$ | Vitride ® 1) | 6 h | 87% |
| 13 | toluene | $ZnEt_2$ | $LiAlH_4$ | 5 h | 85% |

1) Vitride ® = $NaAlH_2(OCH_2CH_2OMe)_2$

EXAMPLE 14 to 27

These examples illustrate the possibility to selectively reduce numerous aldehydes to the corresponding alcohols, without modification of the starting molecule's stereochemistry.

Proceeding as described in example 1, 10 ml of isopropyl ether are charged in the reactor, then 4 mmole of zinc 2-ethyl-hexanoate, then 4 mmole of $NaBH_4$, and finally 0.2 mole of the substrate to be reduced. 0.22 mole of PMHS are then introduced in 1 h under reflux of the solvent. When the substrate has disappeared, hydrolysis of the reaction medium is carried out with 30% aqueous sodium hydroxide, and the alcohol formed is isolated as in example 1.

| Examples | Substrate | Product | Reaction time | Yield (%) |
|---|---|---|---|---|
| 14 | (structure: 3-methyl-2-butenal) | (structure: 3-methyl-2-buten-1-ol) | 3 h | 93% |
| 15 | (structure with CHO) 1) | (structure with $CH_2OH$) | 4 h | 90% |
| 16 | (cyclohexene structure with CHO) | (cyclohexene structure with $CH_2OH$) | 4 h | 95% |

-continued

| Examples | Substrate | Product | Reaction time | Yield (%) |
|---|---|---|---|---|
| 17 | | | 6 h | 87% |
| 18 | | | 5 h | 95% |
| 19 | | | 4 h | 90% |
| 20 | | | 3 h | 94% |
| 21 | | | 4 h | 90% |
| 22 | | | 3 h | 96% |
| 23 | | | 5 h | 80% |
| 24 | | | 4 h | 91% |
| 25 | | | 5 h | 89% |

-continued

| Examples | Substrate | Product | Reaction time | Yield (%) |
|---|---|---|---|---|
| 26 | | | 4 h | 92% |
| 27 | | | 3 h | 97% |

1) The citral used is a 50—50 mixture of geranial and neral

Reduction of Ketones

EXAMPLE 28

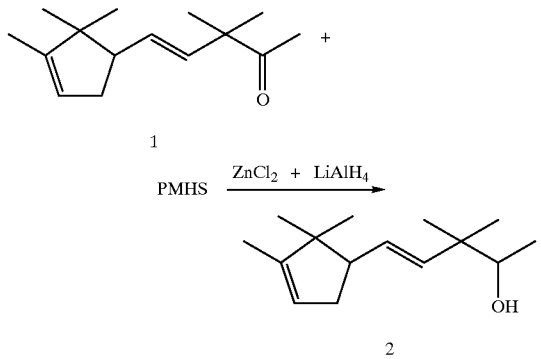

In a three-neck flask of 1 l, 50 g of isopropyl ether, 5 g of $LiAlH_4$ in a 15% toluene solution (0.01 mole), then 1.36 g of zinc chloride (0.01 mole) are introduced and stirred for 15 minutes until the hydrogen release stops. Then, 110 g (0.5 mole) of 3,3-dimethyl-5-(2,2,3-trimethyl-cyclopent-3-en-1-yl)-pent-4-en-2-one (formula 1 above) are introduced, and the reaction medium is taken to reflux. Then 36 g of PMHS (0.55 mole) are introduced in 1 h. The reaction is stirred for 2 additional hours until the GC control indicates that all the substrate had disappeared. The mixture is then cooled to 20°, then 85 g of 45% aqueous potassium hydroxide are added slowly, without letting the temperature of the reaction increase above 40°, and the reaction is kept under stirring for 1 h.

The mixture is decanted, the aqueous phase containing the sodium silicate is separated, then the organic phase is washed with 100 ml of water. The solvent is evaporated and 116 g of product are obtained, the distillation of which on residues gives 105 g of 3,3-dimethyl-5-(2,2,3-trimethyl-cyclopent-3-en-1-yl)-pent-4-en-2-ol (formula 2 above) of purity higher than 98% (yield=95% molar).

EXAMPLE 29 to 37

A 250 ml three-neck flask is charged with 50 ml of isopropyl ether, then 0.4 g of solid sodium borohydride (10 mmole), and 10 mmole of metallic salt or complex, the nature of which is indicated in the table. The mixture is allowed to react for 30 minutes at reflux until the hydrogen release stops, then 50 g of cyclohex-1-en-3-one (0.57 mole) are introduced. 37.2 G of PMHS (0.57 mole) are then introduced in the reaction mixture in 30 minutes and the progress of the reaction is controlled by GC. Hydrolysis of the reaction medium is carried out with 100 g of 30% weight aqueous caustic sodium hydroxide, and the product or products formed are recovered by distillation as in the previous examples.

| Examples | metallic salt 2% molar | Reducing agent 2% molar | Time (hours) | Conversion (%) | Cyclohex-1-en-3-ol Selectivity (%) | Cyclohex-anone (%) Selectivity (%) |
|---|---|---|---|---|---|---|
| 29 | $Mn(2\text{-ethyl-hexanoate})_2$ | $NaBH_4$ | 5 | 95 | 100 | 0 |
| 30 | $Co(2\text{-ethyl-hexanoate})_2$ | $NaBH_4$ | 6 | 97 | 98 | 0 |
| 31 | $Fe(2\text{-ethyl-hexanoate})_2$ | $NaBH_4$ | 8 | 99 | 98 | 0 |
| 32 | $CdCl_2$ | $NaBH_4$ | 5 | 24 | 98 | 2 |
| 33 | $Cu(2\text{-ethyl-hexanoate})_2$ | $NaBH_4$ | 20 | 45 | 1 | 99 |
| 34 | $Ni(2\text{-ethyl-hexanoate})_2$ | $NaBH_4$ | 15 | 96 | 13 | 87 |
| 35 | $PdCl_2(PPh_3)_2$ | $NaBH_4$ | 3 | 99 | 21 | 79 |
| 36 | $RuCl_2(PPh_3)_3$ | $NaBH_4$ | 2 | 92 | 46 | 54 |

-continued

| Examples | metallic salt 2% molar | Reducing agent 2% molar | Time (hours) | Conversion (%) | Cyclohex-1-en-3-ol Selectivity (%) | Cyclohexanone (%) Selectivity (%) |
|---|---|---|---|---|---|---|
| 37 | Cr(2-ethyl-hexanoate)$_2$ | NaBH$_4$ | 14 | 38 | 74 | 22 |

EXAMPLE 38 to 47

We proceeded as described in example 28, operating in isopropyl ether at reflux (68°), but using as catalyst a mixture of 2% molar zinc 2-ethyl-hexanoate, relative to the substrate, and 2% molar of NaBH$_4$. 0.5 Mole of ketonic substrate are used, which are reduced by 0.55 mole of PMHS. When the substrate has disappeared, the hydrolysis is then accomplished with 0.7 mole of 45% aqueous potassium hydroxide. After decantating and evaporation of the solvent, the distillation of the formed alcohol is carried out. The results of the tests indicated in the table show that in all the cases the reduction is accomplished very selectively and with excellent yields, without modification of the starting molecule's stereochemistry.

| Examples | Substrate | Product | Reaction time | Yield (%) |
|---|---|---|---|---|
| 38 | | | 3 h | 97% |
| 39 | | | 4 h | 95% |
| 40 | | | 4 h | 95% |
| 41 | | | 4 h | 94% |
| 42 | | | 3 h | 92% |
| 43 | | | 3 h | 97% |

-continued

| Examples | Substrate | Product | Reaction time | Yield (%) |
|---|---|---|---|---|
| 44 | 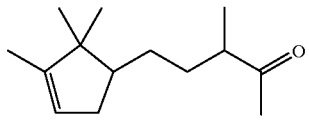 | 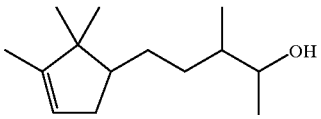 | 4 h | 94% |
| 45 | 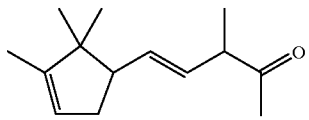 | 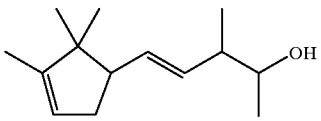 | 4 h | 96% |
| 46 | 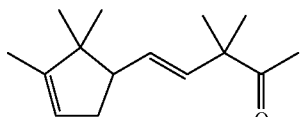 | 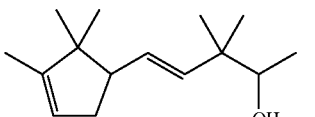 | 5 h | 95% |
| 47 | 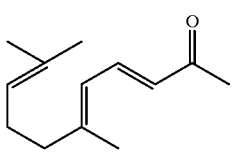 | 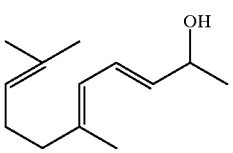 | 4 h | 90% |

Reduction of Esters and Lactones

EXAMPLE 48

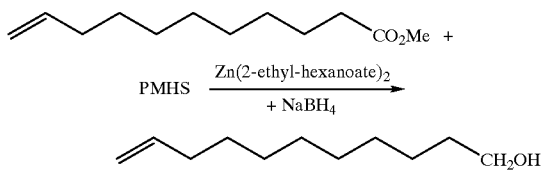

50 G of isopropyl ether, 0.7 g of NaBH$_4$ (0.018 mole), then 1.26 g of zinc 2-ethyl-hexanoate (0.018 mole) are introduced in a 1 l three-neck flask and stirred for 15 minutes until the hydrogen release stops. Then, 120 g (0.6 mole) of methyl 10-undecylenate are added, and the reaction medium is taken to reflux. Then 90 g of PMHS (1.38 mole) are introduced in 1 h. The reaction is stirred for 2 additional hours under reflux at 68° until the GC control indicates that all the substrate has disappeared. The mixture is cooled to 20°, then 300 g of 30% methanolic potassium hydroxide are added slowly under vigourous stirring, and stirring is kept for 1 h. 600 Ml of water are then added, and the mixture is decanted. The aqueous phase containing the sodium silicate is separated, then the organic phase is washed with 100 ml of water. The solvent is evaporated and 104 g of product is obtained, the distillation of which on residues gives 96 g of 10-undecenol with a purity above 98% (yield=94% molar).

EXAMPLE 49 to 61

Operating in isopropyl ether at reflux (68°), we proceed as described in example 48, using as catalyst a mixture of 2% molar of zinc 2-ethyl-hexanoate relative to the substrate and 2% molar of NaBH$_4$. 0.5 Mole of ester or lactone are used and reduced by 1.2 mole of PMHS. When the substrate has disappeared, hydrolysis is then accomplished with 1.7 mole of 45% alcoholic potassium hydroxide. After decantating and evaporation of the solvent, the distillation of the formed alcohol is carried out. The results of the tests in the table indicate that in all the cases the reduction of the esters and lactones is accomplished very selectively and with excellent yields, without modification of the starting molecule's stereochemistry.

| Examples | Substrate | Product | Reaction time | Yield (%) |
|---|---|---|---|---|
| 49 | 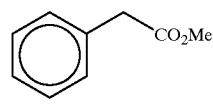 | 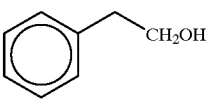 | 3 h | 97% |
| 50 | 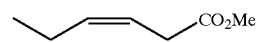 | 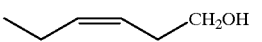 | 4 h | 95% |

-continued

| Examples | Substrate | Product | Reaction time | Yield (%) |
|---|---|---|---|---|
| 51 | 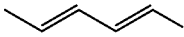 |  | 5 h | 90% |
| 52 |  |  | 8 h | 70% |
| 53 |  |  | 5 h | 85% |
| 54 |  |  | 4 h | 95% |
| 55 |  |  | 5 h | 95% |
| 56 |  |  + $C_6H_{13}OH$ | 4 h | 90% |
| 57 |  |  | 6 h | 94% |
| 58 |  |  | 5 h | 65% |
| 59 |  |  | 5 h | 60% |
| 60 |  |  | 3 h | 93% |
| 61 |  | $HOCH_2(CH_2)_{13}CH_2OH$ | 5 h | 86% |

Triglycerides Reduction

EXAMPLE 62

In a three-neck flask of 1 l, 400 g of toluene are introduced, then 1.2 g of sodium borohydride and 11 g of zinc 2-ethylhexanoate. The mixture is heated to 80° C. during about 30 min, until the hydrogen release stops. Then 200 g of trioleine (glycerol trioleate) are introduced, followed, in 2 hours, by 130 g of PMHS, while keeping the solution at 110° C., the reflux temperature of toluene. The reaction is stirred for 4 additional hours, until the GC analysis of the samples hydrolysed with 30% methanolic potassium hydroxide indicates that the quantity of oleic alcohol formed no longer increases.

The reaction mixture is then poured over 450 g of a 30% methanolic potassium hydroxide solution, keeping the temperature below 40° C., and the reaction is allowed to proceed for 1 additional hour. Then 400 ml of water are added to the solution and the latter is allowed to decant. The organic phase is then separated and the toluene is evaporated. 185 G of a product consisting of oleic alcohol (Z-9-octadecen-1-ol) having a purity of 96% are then distilled under high vacuum (1 mm Hg) at 200–250° C.

EXAMPLE 63

We proceed as in example 62, but using 200 g of peanut oil. 120 G of a mixture consisting of 14% of 1-hexadecanol, 55% of oleic alcohol and 17% of linoleic alcohol (Z,Z-9,12-octadecadien-1-ol) are obtained by distillation.

EXAMPLE 64

We proceed as in example 62, but using 200 g of sunflower oil. 110 G of a mixture formed of 12% of 1-hexadecanol, 35% of oleic alcohol and 40% of linoleic alcohol (Z,Z-9,12-octadecadien-1-ol) are obtained by distillation.

EXAMPLE 65

We proceed as in example 62, but using 200 g of linseed oil. 110 G of a mixture formed of 5% of 1-hexadecanol, 18% of oleic alcohol, 17% of linoleic alcohol (Z,Z-9,12-octadecadien-1-ol) and. 52% of linolenic alcohol (Z,Z,Z-9,12,15-octadecatrien-1-ol) are obtained by distillation.

EXAMPLE 66

We proceed as in example 62, but using 200 g of colza oil. 110 G of a mixture formed of 58% of oleic alcohol, 20% of linoleic alcohol (Z,Z-9,12-octadecadien-1-ol) and 8% of linolenic alcohol (Z,Z,Z-9,12,15-octadecatrien-1-ol) are obtained by distillation.

What is claimed is:

1. A reductive system, consisting essentially of the product of:
    a) an effective amount of polymethylhydroxysilane (PMHS) to effect reduction of a carbonylated substrate to an alcohol, and
    b) an effective amount of catalyst to catalyze said reduction, said catalyst consisting essentially of the reaction product of
        i) a metallic salt or complex according to the general formula $MX_n$, wherein M is a transition metal selected from the group consisting of zinc, cadmium, manganese, cobalt, iron, copper, nickel, ruthenium and palladium, X is an anion or an anionic ligand, and n is a number from 1 to 4, and
        ii) a reducing agent selected from the group consisting of lithium hydride, sodium hydride, potassium hydride, an alkaline earth metal hydride, a boron hydride, a metallic borohydride, an alkylborane, an alkoxyborane, an aluminum hydride, an organic magnesium compound and an organic lithium compound.

2. A reductive system capable of being mixed together with polymethylhydroxysilane to effect reduction of a carbonylated substrate to an alcohol, consisting essentially of:
    a) an effective amount of a catalyst to catalyze reduction of a carbonylated substrate to an alcohol, said catalyst consisting essentially of the reaction product of
        i) a metallic salt or complex according to the general formula $MX_n$, wherein M is a transition metal selected from the group consisting of zinc, cadmium, manganese, cobalt, iron, copper, nickel, ruthenium and palladium, X is an anion or an anionic ligand, and n is a number from 1 to 4, and
        ii) a reducing agent; and
    b) the carbonylated substrate to be reduced by the polymethylhydroxysilane after its addition and catalyzed by said catalyst as pacified above.

3. Reductive system according to claim 1 or 2 wherein X is a halide or carboxylate.

4. Reductive system according to claim 1 or 2, wherein the concentration of said catalyst, expressed in molar percent of metal relative to said substrate, is between 0.1 and 10%.

5. Reductive system according to claim 1 or 2, wherein PMHS is employed in approximately stoichiometric amounts relative to said substrate.

6. Reductive system according to claim 1 or 2, wherein said catalyst is provided in a molar ratio of reducing agent relative to metal of between about 1 and 2.

7. Reductive system according to claim 1 or 2, wherein the transition metal in the metallic salt or complex is zinc, manganese, cobalt or iron.

8. Reductive system according to claim 1 or 2, wherein the reducing agent is sodium borohydride.

9. Reductive system according to claim 1 or 2, wherein the anion in the metallic salt or complex is selected from the group consisting of chloride, bromide, iodide, carbonate, isocyanate, cyanate, sulfate, phosphate, acetate, propionate, 2-ethylhexanoate, stearate and naphthenate.

10. Reductive system according to claim 1 or 2, wherein a complexing agent is provided for the metallic hydride that is formed.

11. Reductive system according to claim 10, wherein the complexing agent is selected from the group consisting of ether alcohols and amine alcohols.

12. Reductive system according to claim 11, wherein the complexing agent is methoxyethanol, dimethylaminomethanol, dimethylaminoethanol, diethanolamine or triethanolamine.

13. Reductive system according to claim 7, wherein the metallic salt or complex is $Zn(2\text{-ethylhexanoate})_2$, $Mn(2\text{-ethylhexanoate})_2$, $Co(2\text{-ethylhexanoate})_2$ or $Fe(2\text{-ethylhexanoate})_2$ and the reducing agent is sodium borohydride.

14. Reductive system according to claim 2, wherein the reducing agent is selected from the group consisting of lithium hydride, sodium hydride, potassium hydride, an alkaline earth metal hydride, a boron hydride, a metallic borohydride, an alkylborane, an alkoxyborane, an aluminum hydride, an organic magnesium compound and an organic lithium compound.

15. Reductive system according to claim 1 or 2, wherein said substrate which is reduced to its corresponding alcohol is an aldehyde, ketone, ester, or lactone.

16. Reductive system according to claim 15, wherein the substrate which is reduced into its corresponding alcohol is an aldehyde selected from the group consisting of linear or branched butanal, pentanal, hexanal, heptanal, octanal, decanal or dodecanal, acroleine, methacroleine, crotonaldehyde, prenal, citral, retinal, campholenic aldehyde, cinnamic aldehyde, hexylcinnamic aldehyde, formyl pinane, nopal, benzaldehyde, cuminic aldehyde, vanilline and salicylic aldehyde.

17. Reductive system according to claim 15, wherein the substrate which is reduced into its corresponding alcohol is a ketone selected from the group consisting of hexan-2-one, octan-2-one, nonan-4-one, dodecan-2-one, methyl vinyl ketone, mesityl oxyde, acetophenone, cyclopentanone, cyclohexanone, cyclododecanone, cyclohex-1-en-3-one, isophorone, oxophorone, carvone and camphor.

18. Reductive system according to claim 15, wherein the substrate which is reduced into its corresponding alcohol is an ester or a lactone selected from the group consisting of the acetates, propionates, butyrates, isobutyrates, alkyl or aryl benzoates, acrylates, alkyl or aryl crotonates, alkyl cinnamates, methyl cis-3-hexenoate, methyl sorbate, methyl salicylate, methyl 10-undecylenate, methyl oleate, methyl linoleate, methyl linolenate, any mixture of natural fatty acid esters, caprolactone butyrolactone, dodecalactone, diketene and sclareolide.

19. A catalyst system capable of being reacted together to effect reduction of a carbonylated substrate to an alcohol by polymethylhydroxysilane, said catalyst consisting essentially of a mixture of:
   a) a metallic salt or complex according to the general formula $MX_n$, wherein M is a transition metal selected from the group consisting of zinc, cadmium, manganese, cobalt, iron, copper, nickel, ruthenium and palladium, X is an anion or an anionic ligand, and n is a number from 1 to 4, and
   b) a reducing agent selected from the group consisting of lithium hydride, sodium hydride, potassium hydride, an alkaline earth metal hydride, a boron hydride, a metallic borohydride, an alkylborane, an alkoxyborane, an aluminum hydride, an organic magnesium compound and an organic lithium compound.
wherein components a) and b) upon being reacted together form said catalyst which is effective to catalyze said reduction.

20. Catalyst according to claim 19 wherein X is a halide or carboxylate.

21. Catalyst according to claim 19, wherein the ratio of reducing agent relative to metal is between 1 and 2.

22. Catalyst according to claim 19, wherein the transition metal is zinc, manganese, cobalt or iron.

23. Catalyst according to claim 19, wherein X is selected from the group consisting of chloride, bromide, iodide, carbonate, isocyanate, cyanate, sulfate, phosphate, acetate, propionate, 2-ethylhexanoate, stearate and naphthenate.

24. Catalyst according to claim 19, wherein the reducing agent is sodium borohydride.

25. Catalyst according to claim 24, wherein the metallic salt or complex is $Zn(2\text{-ethylhexanoate})_2$, $Mn(2\text{-ethylhexanoate})_2$, $Fe(2\text{-ethylhexanoate})_2$ or $Co(2\text{-ethylhexanoate})_2$ and the reducing agent is sodium borohydride.

26. Catalyst according to claim 19, further comprising a complexing agent.

27. Catalyst according to claim 26, wherein the complexing agent is selected from the group consisting of ether alcohols and amine alcohols.

28. Catalyst according to claim 27, wherein the complexing agent is selected from the group consisting of methoxyethanol, dimethylaminomethanol, dimethylaminoethanol, diethanolamine and triethanolamine.

29. A reaction product produced by a catalyzed polymethylhydroxysilane reduction of a carbonylated substrate to an alcohol before recovery of the alcohol by hydrolysis, consisting essentially of:
   a) a catalyst, said catalyst consisting essentially of the reaction product of
      i) a metallic salt or complex according to the general formula $MX_n$, wherein M is a transition metal selected from the group consisting of zinc, cadmium, manganese, cobalt, iron, copper, nickel, ruthenium and palladium, X is an anion or an anionic ligand, and n is a number from 1 to 4, and
      ii) a reducing agent selected from the group consisting of lithium hydride, sodium hydride, potassium hydride, an alkaline earth metal hydride, a boron hydride, a metallic borohydride, an alkylborane, an alkoxyborane, an aluminum hydride, an organic magnesium compound and an organic lithium compound, and
   b) the reaction product of a carbonylated substrate and a polymethylhydroxysilane (PMHS).

30. Product according to claim 29, wherein the transition metal is zinc, manganese, cobalt or iron.

31. Product according to claim 29, wherein the reducing agent is sodium borohydride.

32. Product according to claim 29, wherein the concentration of said catalyst, expressed in molar percent of metal relative to said substrate, is between about 0.1 and 10%.

33. Product according to claim 29, wherein said catalyst is provided in a molar ratio of reducing agent relative to metal of between about 1 and 2.

34. Product according to claim 29, wherein PMHS is employed in approximately stoichiometric amounts relative to said substrate.

35. Reaction product according to claim 29, wherein X is selected from the group consisting of chloride, bromide, iodide, carbonate, isocyanate, cyanate, sulfate, phosphate, acetate, propionate, 2-ethylhexanoate, stearate and naphthenate.

36. Reaction product according to claim 29, wherein the metallic salt or complex is $Zn(2\text{-ethylhexanoate})_2$, $Mn(2\text{-ethylhexanoate})_2$, $Co(2\text{-ethylhexanoate})_2$ or $Fe(2\text{-ethylhexanoate})_2$ and the reducing agent is sodium borohydride.

37. Reaction product according to claim 29, wherein the carbonylated substrate which is reduced to its corresponding alcohol is an aldehyde, ketone, ester or lactone.

38. Reductive product according to claim 37, wherein the substrate which is reduced into its corresponding alcohol is an aldehyde selected from the group consisting of linear or branched butanal, pentanal, hexanal, heptanal, octanal, decanal or dodecanal, acroleine, methacroleine, crotonaldehyde, prenal, citral, retinal, campholenic aldehyde, cinnamic aldehyde, hexylcinnamic aldehyde, formyl pinane, nopal, benzaldehyde, cuminic aldehyde, vanilline and salicylic aldehyde.

39. Reductive product according to claim 37, wherein the substrate which is reduced into its corresponding alcohol is a ketone selected from the group consisting of hexan-2-one, octan-2-one, nonan-4-one, dodecan-2-one, methyl vinyl ketone, mesityl oxyde, acetophenone, cyclopentanone, cyclohexanone, cyclododecanone, cyclohex-1-en-3-one, isophorone, oxophorone, carvone and camphor.

40. Reductive product according to claim 37, wherein the substrate which is reduced into its corresponding alcohol is an ester or a lactone selected from the group consisting of the acetates, propionates, butyrates, isobutyrates, alkyl or aryl benzoates, acrylates, alkyl or aryl crotonates, alkyl cinnamates, methyl cis-3-hexenoate, methyl sorbate, methyl salicylate, methyl 0-undecylenate, methyl oleate, methyl linoleate, methyl linolenate or any mixture of natural fatty acid esters, caprolactone butyrolactone, dodecalactone, diketene and sclareolide.

* * * * *

UNITED STATES PATENT AND TRADEMARK OFFICE
CERTIFICATE OF CORRECTION

PATENT NO. : 6,046,127
DATED : April 4, 2000
INVENTOR(S) : Hubert Mimoun

It is certified that error appears in the above-identified patent and that said Letters Patent is hereby corrected as shown below:

On the title page under the section heading "Related U.S. Application Data": change "Division" to --Continuation--.

Column 1,
Line 4: change "divisional" to --continuation--.

Column 20,
Line 10: change "pacified" to --specified--.

Column 22,
Line 62: change "O-undecyclenate," to --10-undecyclenate,--.

Signed and Sealed this

Tenth Day of July, 2001

*Attest:*

Nicholas P. Godici

NICHOLAS P. GODICI
*Acting Director of the United States Patent and Trademark Office*

*Attesting Officer*